United States Patent
Rhodes et al.

(10) Patent No.: US 7,468,041 B2
(45) Date of Patent: Dec. 23, 2008

(54) MODULAR SURGICAL INSTRUMENT WITH RECIPROCABLE IMPLEMENT

(75) Inventors: James M. Rhodes, Warsaw, IN (US); Oscar F. Salcido, Mentone, IN (US); Herbert E. Schwartz, Ft Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 816 days.

(21) Appl. No.: 10/606,533

(22) Filed: Jun. 26, 2003

(65) Prior Publication Data
US 2004/0267164 A1   Dec. 30, 2004

(51) Int. Cl.
*A61B 10/00* (2006.01)

(52) U.S. Cl. .............. 600/564; 600/562; 600/563; 600/565; 600/566; 600/567; 600/568

(58) Field of Classification Search .......... 600/562, 600/563, 564, 565, 566, 567, 568
See application file for complete search history.

(56) References Cited

U.S. PATENT DOCUMENTS

| | | | |
|---|---|---|---|
| 4,091,880 A * | 5/1978 | Troutner et al. ............ 173/163 |
| 4,411,653 A * | 10/1983 | Razi ........................ 604/157 |
| 4,662,371 A | 5/1987 | Whipple et al. |
| 4,834,092 A | 5/1989 | Alexson et al. |
| 4,848,338 A * | 7/1989 | De Satnick et al. ........... 606/1 |
| 4,863,088 A * | 9/1989 | Redmond et al. ............ 227/19 |
| 4,963,147 A | 10/1990 | Agee et al. |
| 5,006,123 A * | 4/1991 | Soll et al. .................. 606/166 |
| 5,334,198 A * | 8/1994 | Hart et al. .................. 606/52 |
| 5,507,772 A | 4/1996 | Shutt et al. |
| 5,618,304 A | 4/1997 | Hart et al. |
| 5,782,834 A | 7/1998 | Lucey et al. |
| 5,843,091 A * | 12/1998 | Holsinger et al. ........... 606/108 |
| 5,928,252 A | 7/1999 | Steadman et al. |
| 5,961,538 A | 10/1999 | Pedlick et al. |
| 6,126,674 A * | 10/2000 | Janzen ...................... 606/206 |
| 6,179,791 B1 * | 1/2001 | Krueger ..................... 600/587 |
| 6,277,083 B1 * | 8/2001 | Eggers et al. ............... 600/564 |
| 6,319,258 B1 | 11/2001 | Mc Allen, III et al. |
| 6,331,166 B1 * | 12/2001 | Burbank et al. ............ 600/567 |

(Continued)

OTHER PUBLICATIONS

Shahriaree, Heshmat, M.D., et al., O'Connor's Textbook of Arthroscopic Surgery, 2nd Edition, Chapter 19, Arthroscopic Instrumentation, pp. 231 and 238, © 1992, J.B. Lippencott Company, Philadelphia, Pennsylvania.

*Primary Examiner*—Max Hindenburg
*Assistant Examiner*—Jeffrey G Hoekstra (57) ABSTRACT

Surgical instruments for use in minimally invasive surgery are described. The instruments have parts that are easily separable and easily assembled. A reciprocal slide member is operable by a cam portion of a lever received in a slot in the slide member. There is no mechanical connection between the lever and the slide member. The slide member is connected to elongate surgical implement components that extend through an elongate support member. The elongate surgical implement components are capable of reciprocal movement in the proximal-distal direction. In some embodiments, the elongate surgical implements can be used for measuring distances arthroscopically; these surgical implements can have beveled ends for more precise measurement of distances. The surgical instrument can be modular, with separate tool and actuator modules. The surgical instrument can be used with any implement that can be operated by reciprocal motion.

19 Claims, 9 Drawing Sheets

U.S. PATENT DOCUMENTS

| | | |
|---|---|---|
| 6,427,351 B1 | 8/2002 | Matthews et al. |
| 6,547,798 B1 * | 4/2003 | Yoon et al. .................. 606/141 |
| 2005/0192598 A1 * | 9/2005 | Johnson et al. ............. 606/148 |
| 2006/0161190 A1 * | 7/2006 | Gadberry et al. ............ 606/174 |
| 2006/0241723 A1 * | 10/2006 | Dadd et al .................... 607/57 |

* cited by examiner

MODULAR SURGICAL INSTRUMENT WITH RECIPROCABLE IMPLEMENT

FIELD OF THE INVENTION

The present invention relates to surgical instruments and more particularly to the provision of Minimally Invasive Surgery (MIS) surgical instruments with parts that are easily separable for cleaning and sterilizing and repair or replacement.

BACKGROUND OF THE INVENTION

Various types of MIS are being performed by surgeons, including laparascopy, endoscopy and arthroscopy surgery. In arthroscopy, small incisions are made at the affected joint to form portals for the insertion of instruments, including a small lens and lighting system (an arthroscope). The arthroscope is connected to a viewing device, such as a television camera to allow the surgeon to see the interior of the joint. Other instruments are inserted through other portals to perform a variety of tasks. For example, the surgical instrument may include an implement for manipulating native tissue (for example, tissue grasping, tissue cutting, bone abrading), or an implement for introducing and implanting a therapeutic device.

Typical surgical instruments used in arthroscopic procedures include rongeurs, such as the Kerrison rongeur, punch forceps, basket forceps, suction punches and cup curet, for example. Examples of arthroscopic instruments are described and illustrated in O'Connor's Textbook of Arthroscopic Surgery, $2^{nd}$ ed., 1992, Chapter 19.

In many surgical settings, it is often necessary for the surgeon to make measurements between two points. Due to the confined spaces of arthroscopic surgery, measuring such distances is often quite difficult, particularly when the measurement needed is larger than the size of the incision or transverse to the direction of the incision. Arthroscopic knee surgery provides many such situations. For example, it may be helpful if a surgeon could measure the size of a defect in the meniscus of a knee, to aid in choosing the appropriate method to repair the defect.

An arthroscopic measuring device is disclosed in U.S. Pat. No. 6,427,351B1, which is incorporated by reference herein in its entirety. The device disclosed in that patent provides a handle and an extension. The extension has a distal tip for intraoperative insertion into the body through an incision. Two wires extend from a block in the handle through passageways in two separate tubes that comprise the extension. The block is connected to an actuator element. The actuator elements disclosed can be moved back and forth in a direction parallel to the longitudinal axis of the handle to move the wires out of and into the tubes. At their distal ends, the tubes diverge at a fixed angle so that the distance between the ends of the wires increases as the wires are pushed further outward and decreases as the wires are pulled back into the handle. Calibrations on the handle correspond with the distance between the ends of the wires so that the surgeon can determine one or more of the dimensions of a defect in the bone, cartilage or other soft tissue.

Although the arthroscopic measuring device disclosed in U.S. Pat. No. 6,427,351B1 provides a useful surgical tool, operation of the actuating mechanism disclosed can be difficult for the surgeon, particularly due to friction as the wires are pushed through the divergent tube endings. In addition, use of that device may require that the surgeon use both hands to hold the handle and move the actuating mechanism.

SUMMARY OF THE INVENTION

The present invention comprises a surgical instrument for use within confined spaces, such as within an arthroscopic surgical site.

In one aspect, the present invention provides a surgical instrument having a proximal end and a distal end. The instrument comprises a handle at the proximal end. The handle includes a grip portion. The instrument also comprises a hollow elongate support member extending distally from the handle. The hollow elongate support member has a distal end at the distal end of the instrument. A slide member has a proximal end and a distal end and a slot between the two ends; the slot of the slide member extends in a proximal-distal direction. A lever is pivotally connected to the handle. The lever includes a grip portion on one side of the pivotal connection and an integral drive portion on the other side of the pivotal connection. At least part of the drive portion of the lever comprises an integral cam received in the slot in the slide member. The surgical instrument includes a surgical implement that has a proximal end connected to the distal end of the slide member, an elongate portion extending through the hollow elongate support, and a distal end. The surgical instrument also includes a spring to urge the slide member toward the proximal end of the instrument. The slide member and elongate portion of the surgical implement are capable of being moved reciprocally in a linear proximal-distal direction by pivoting the lever. The surgical instrument is free of any mechanical connection between the lever and the slide member.

In another aspect, the present invention provides a modular surgical instrument. The modular surgical instrument comprises an actuator module and a tool module. The actuator module comprises a handle and a lever. The handle includes a grip portion and an integral support portion. The support portion of the handle has proximal and distal ends and a support surface between the proximal and distal ends. The handle is substantially open above the support surface. The lever is pivotally connected to the support portion of the handle. The lever includes a trigger portion and a drive portion. The trigger portion is longer than the drive portion. The drive portion extends through an opening in the support surface of the handle. The tool module comprises a hollow housing having proximal and distal ends and a hollow elongate support member fixed to the distal end of the housing. The elongate support member of the tool module extends outwardly from the housing to a free distal end. There is an opening at the free distal end of the elongate support member. The housing and elongate support member define an open passageway between them. The tool module also includes a surgical implement capable of reciprocal motion in the proximal-distal direction relative to the hollow elongate support member. At least part of the surgical implement extends through the hollow elongate support member and out through the opening at the free distal end of the elongate support member. The tool module also includes a slide member operably connected to at least part of the surgical implement. The slide member is capable of reciprocal motion in the proximal-distal direction relative to the housing. The slide member has a drive surface. The actuator module and tool module are capable of being assembled and disassembled so that at least one of the modules can be reused independent of the other module. When the actuator module and tool module are assembled, the drive portion of the lever engages the drive surface of the slide member so that the slide member and surgical implement can be moved in the distal direction by squeezing the trigger portion of the lever.

In another aspect, the present invention provides a disposable surgical tool module for use with a separate actuator module. The surgical tool module comprises a housing having proximal and distal ends. The tool modules also comprises a hollow elongate support member at the distal end of the housing. The hollow elongate support member extends outwardly from the housing to a free distal end. The free distal end of the elongate support has an opening. The tool module also includes a surgical implement capable of reciprocal motion in the proximal-distal direction. At least part of the surgical implement extends through the hollow elongate support member and out through the opening at the free distal end of the elongate support member. A slide member is operably connected to at least part of the surgical implement and is capable of reciprocal motion in the proximal and distal directions. The slide member has a slot. The housing has an opening aligned with the slot of the slide member. The tool module is free from any structure for moving the slide member in the proximal direction.

In another aspect, the present invention provides a surgical instrument having proximal and distal ends. The surgical instrument comprises a handle at the proximal end. The handle includes a grip portion. A hollow elongate support member extends outward from the handle in a distal direction. The surgical instrument also includes a surgical implement extending through the elongate support member and capable of reciprocating in the proximal-distal direction in the elongate support member. A lever is pivotally connected to the handle. The lever includes a trigger portion and a drive portion. The trigger portion of the lever is longer than the drive portion. The lever extends through an opening in the handle. A slide member has a drive surface engaging the drive portion of the lever. The slide member is capable of reciprocal motion in the proximal-distal direction. The surgical implement may includes a pair of elongate substantially flexible distance references connected at one end to the slide member and extending out of the distal end of the elongate support member. The elongate support member has a substantially cylindrical portion and a pair of discrete elongate tubes extending from the substantially cylindrical portion to beveled distal ends. The discrete elongate tubes have substantially parallel portions and curved divergent portions. One of the elongate substantially flexible distance references extends through one of the discrete elongate tubes and the other elongate substantially flexible distance reference extends through the other of the discrete elongate tubes. Each elongate substantially flexible distance reference has a beveled distal end.

In another aspect, the present invention provides a surgical instrument having a proximal end and a distal end. The instrument comprises a handle at the proximal end. The handle includes a grip portion. The instrument also comprises a hollow elongate support member extending distally from the handle. The hollow elongate support member has a distal end at the instrument's distal end. A slide member has a proximal end and a distal end and a slot between the two ends; the slot of the slide member extends in a proximal-distal direction. A lever is pivotally connected to the handle. The lever includes a grip portion on one side of the pivotal connection and an integral drive portion on the other side of the pivotal connection. At least part of the drive portion of the lever comprises an integral cam received in the slot in the slide member. The surgical instrument includes a surgical implement has a proximal end connected to the distal end of the slide member, an elongate portion extending through the hollow elongate support, and a distal end. The surgical instrument also includes a spring to urge the slide member toward the proximal end of the instrument. The slide member and elongate portion of the surgical implement are capable of being moved reciprocally in a linear proximal-distal direction by pivoting the lever. The elongate support member has a substantially cylindrical portion and a non-cylindrical distal end. The distal end of the elongate support member has substantially flat upper and lower surfaces and an interior wedge between the substantially flat upper and lower surfaces. The interior wedge diverges in the distal direction and defines two divergent passageways. One of the elongate substantially flexible distance references extends through one of the divergent passageways of the elongate support member and the other of the elongate substantially flexible distance references extends through the other of the divergent passageways of the elongate support member.

Additional features of the present invention will become apparent to those skilled in the art upon consideration of the following detailed description of preferred embodiments exemplifying the best mode of carrying out the invention as presently perceived.

DETAILED DESCRIPTION

Figure 8:
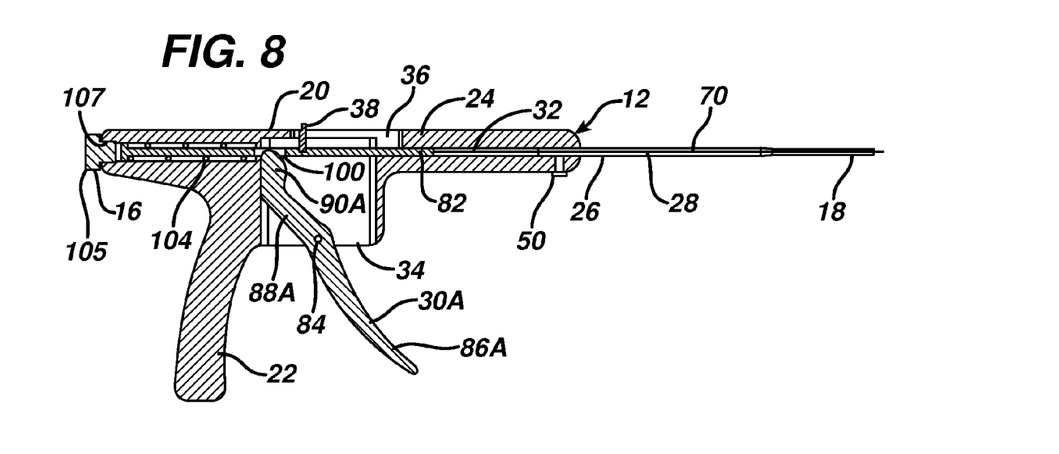
FIG. 8 is a cross-section of another embodiment of an instrument embodying the principles of the present invention.
Figure 18:
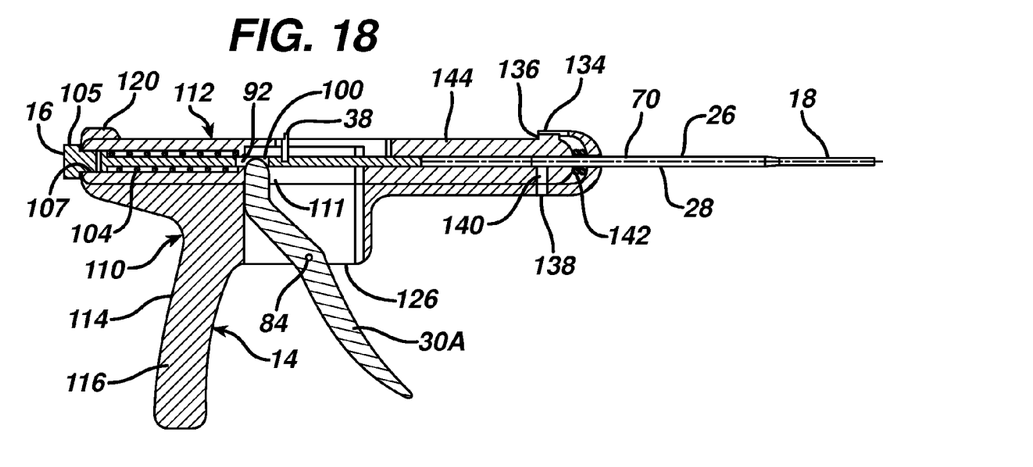
FIG. 18 is a cross-section of an assembly of the actuator module of FIG. 16 and the tool module of FIG. 17.

FIGS. 1-6 show a first embodiment 10 of a surgical instrument embodying the principles of the present invention. A second embodiment of the surgical instrument is shown in FIG. 8 and is designated 12. A third modular embodiment is illustrated in FIG. 18 and is designated 14. In all three illustrated surgical instruments 10, 12, 14, the instrument has a proximal end 16 and a distal end 18.

In the first illustrated instrument 10, the instrument has a handle 20 at the proximal end 16. The handle 20 includes a grip portion 22 and a body portion 24. The first illustrated instrument 10 also has a hollow elongate support member 26, a surgical implement 28, and a lever 30.

Figure 2:
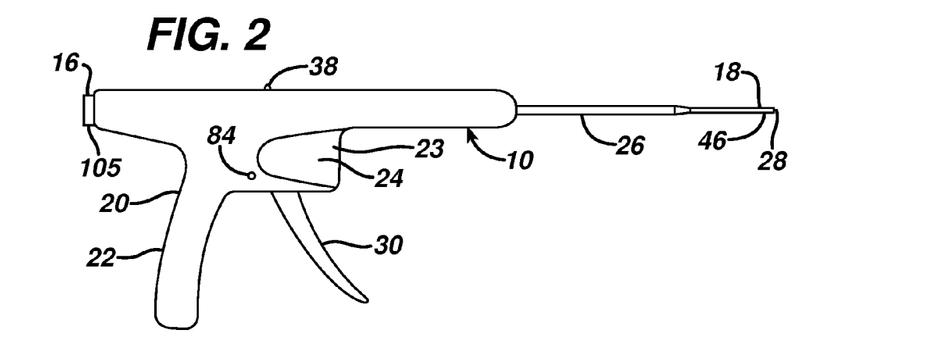
FIG. 2 is an elevation or side view of the instrument of FIG. 1, with the lever in its at rest position.
Figure 4:
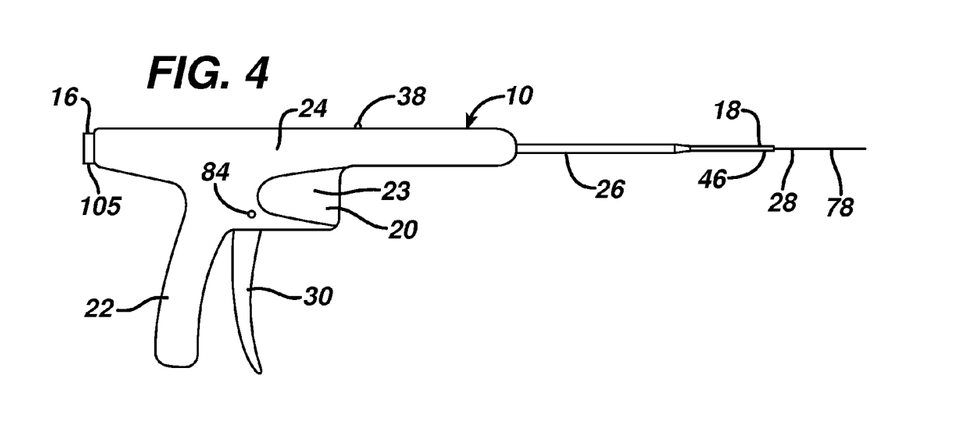
FIG. 4 is an elevation or side view similar to FIG. 2, except showing the lever in a squeezed position to extend the flexible distance references further out of the distal end of the instrument.

The exterior of the handle 20 may have recessed contours, such as that shown at 23 in FIGS. 2 and 4 for the surgeon's fingers so that the surgeon can more easily grasp the handle.

Figure 1:
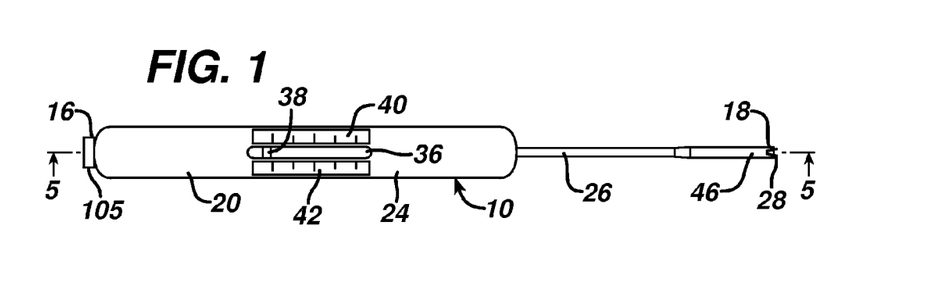
FIG. 1 is a top plan view of an MIS surgery instrument of this invention, with the lever in its at rest position.
Figure 3:
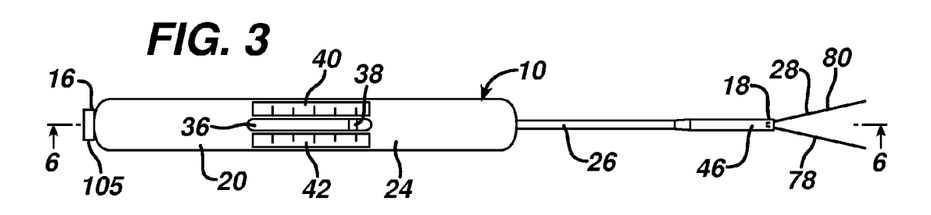
FIG. 3 is a top plan view similar to FIG. 1, except showing the lever in a squeezed position to extend the flexible distance references further out of the distal end of the instrument.
Figure 5:
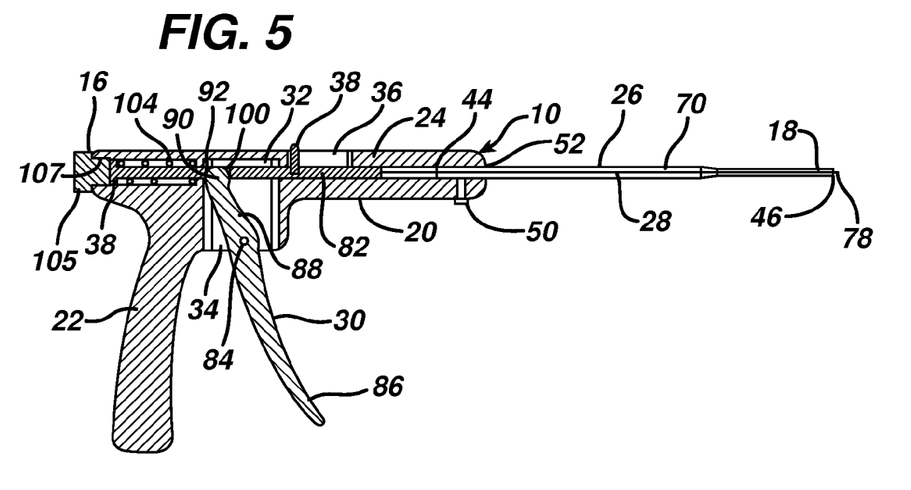
FIG. 5 is a cross-section of the instrument of FIGS. 1-2, taken along line 5-5 of FIG. 1, with the lever in its at rest position.
Figure 6:
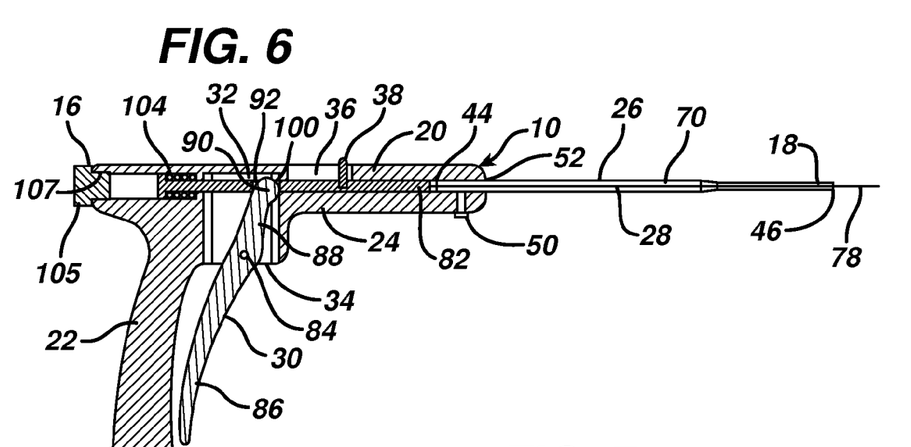
FIG. 6 is a cross-section of the instrument of FIGS. 3-4, taken along line 6-6 of FIG. 3, showing the lever in its squeezed position.

The interior of the body portion 24 of the handle 20 of the first illustrated instrument 10 is shown in FIGS. 5-6. As there shown, the body portion 24 defines an elongate channel 32 running in a proximal-distal direction. The underside of the body portion 24 of the handle 20 has an entry slot or opening 34 to receive the lever 30. As shown in FIGS. 1 and 3, the top side of the body portion 24 of the handle has a slot or opening 36 to receive a movable measuring indicator pin 38. Adjacent the top slot or opening 36 and the indicator pin 38, the top surface of the handle includes fixed measuring indicia 40, 42 (shown in FIGS. 1 and 3). The fixed measuring indicia 40, 42 comprise a series of spaced marks at intervals such as 1 mm, for example. Generally, the measuring indicia provide a scale for measuring distances of, for example, 1-20 mm; the length of the slot or opening 36 is sufficient to allow the indicator pin 38 to move along substantially the entire length of the scale provided by the fixed measuring indicia 40, 42. It should be understood that the features described in this paragraph are provided for purposes of illustration only; the present invention is not limited to the provision of such slots, such an indicator pin, or such measuring indicia unless expressly called for in the claims. In addition, the 1-20 mm scale described above is provided as an example only; the invention is not limited to any particular scale, range of motion for an indicator pin, or size of slot unless expressly called for in the claims.

Figure 9:
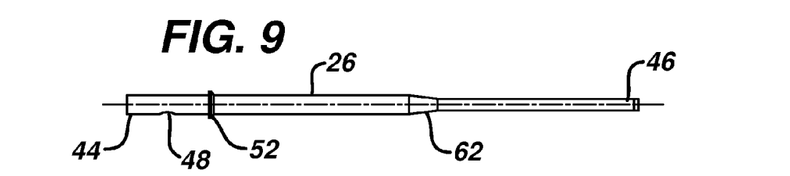
FIG. 9 is an elevation or side view of the elongate support member of the instruments illustrated in FIGS. 1-6.
Figure 10:
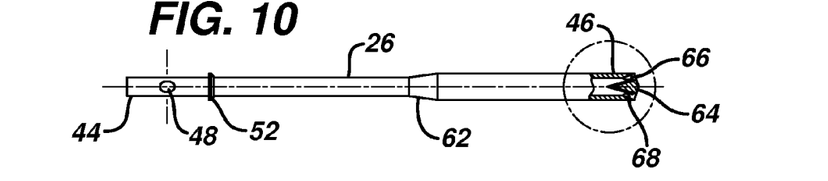
FIG. 10 is a bottom plan view of the elongate support member of FIG. 9.

As shown in FIGS. 5-6, the hollow elongate support 26 of the first illustrated instrument 10 has a proximal end 44 and a distal end 46. The proximal end 44 of the hollow elongate support 26 is received within the body portion 24 of the handle 20. As shown in FIGS. 9-10, the illustrated elongate support 26 has a socket 48 near its proximal end 44. The socket may comprise an indentation or a hole, for example. As shown in FIGS. 5-6, when the proximal end 44 is received within the body 24 of the handle 20, a screw 50 is inserted through the body 24 to secure the elongate support 26 in position. It should be understood that other structures, such as a ball-spring device, could be used instead of a screw to secure the position of the elongate support 26. The illustrated elongate support 26 also has a fixed annular stop 52, shown in FIGS. 9-10, to ensure that the elongate support is properly positioned on the handle body 24.

Figure 11:
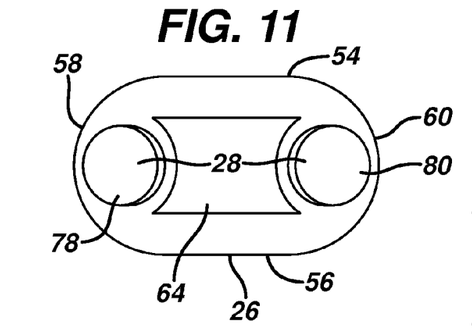
FIG. 11 is an enlarged end view of the distal end of the elongate support member of FIGS. 9-10.

Throughout most of its length from the proximal end 44, the elongate support 26 of the first illustrated instrument 10 is substantially cylindrical in shape, with a diameter of about 0.188 inches (4.8 mm). The shape of the first illustrated elongate support 26 changes between the fixed annular stop 52 and the distal end 46. At the distal end 46, the first elongate support has flat upper and lower surfaces 54, 56 joined by curved surfaces 58, 60, as shown in FIG. 11. The distal end 46 is non-cylindrical, with a width or transverse dimension of about 5 mm in the illustrated embodiment and a thickness of about 3 mm. The maximum transverse dimension of the distal end is greater than the diameter of the cylindrical portion, and is preferably sized to fit within standard arthroscopic cannulae.

As shown in FIGS. 9-10, the cylindrical proximal portion and non-cylindrical distal end portion are joined by a transition section 62. The transition section 62 is cylindrical where it joins the proximal cylindrical portion and shaped like the distal non-cylindrical portion where they join.

Figure 7:
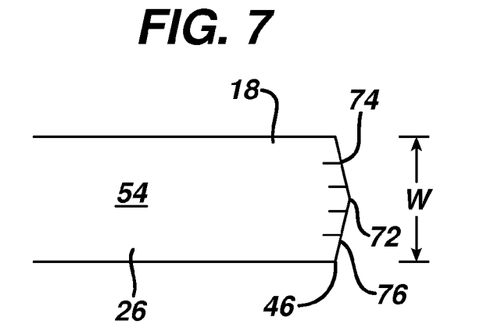
FIG. 7 is a top detail view of the distal end of the elongate support member of the instrument of FIGS. 1-6.

As shown in FIG. 7, the upper surface 54 of the distal end 46 of the elongate support 26 may include distance indicia, such as markings at 1 mm intervals, to assist the surgeon in measuring defects during arthroscopic surgery.

Figure 12:
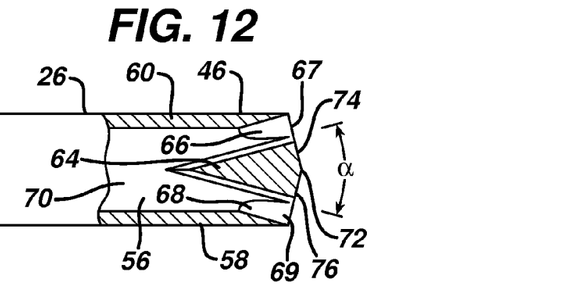
FIG. 12 is an enlarged top plan view of the distal end of the elongate support member of FIGS. 9-11, with part shown in cross-section.

As shown in FIG. 12, the first instrument 10 includes an interior wedge 64 at the distal end of the elongate support member 26 between the upper and lower surfaces 54, 56. The interior wedge 64 diverges in the distal direction and defines two divergent passageways 66, 68 leading to spaced distal openings 67, 69. The interior wedge defines an angle α, shown in FIGS. 12 and 19. The angle α may be, for example, between 30-45° so that the divergent passageways 66, 68 are at that angle. Proximal to the two passageways 66, 68 defined by the interior wedge 64, the elongate support member provides a single common channel 70.

Figure 19:
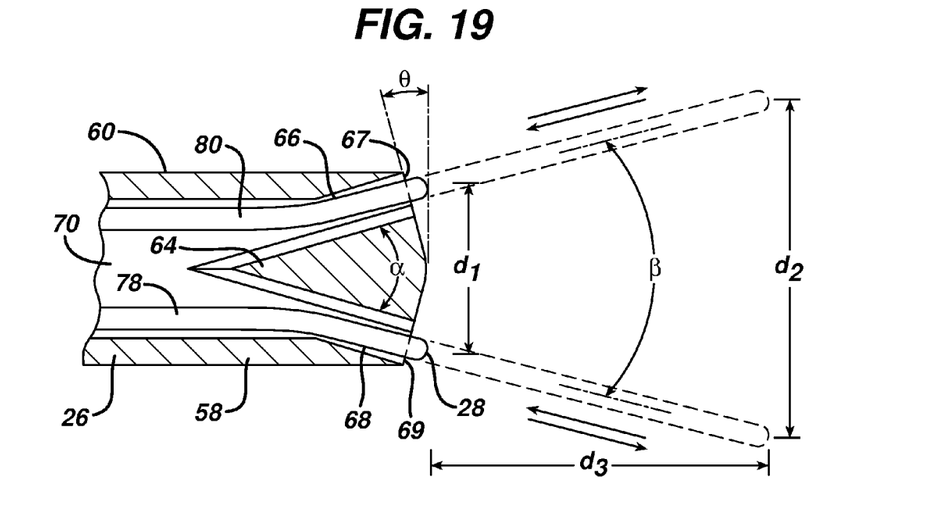
FIG. 19 is a cross-section of the distal end of one possible tool module for the modular instrument of FIG. 18, with the extended position of the surgical implement shown in solid and the extended position shown in phantom.
Figure 20:
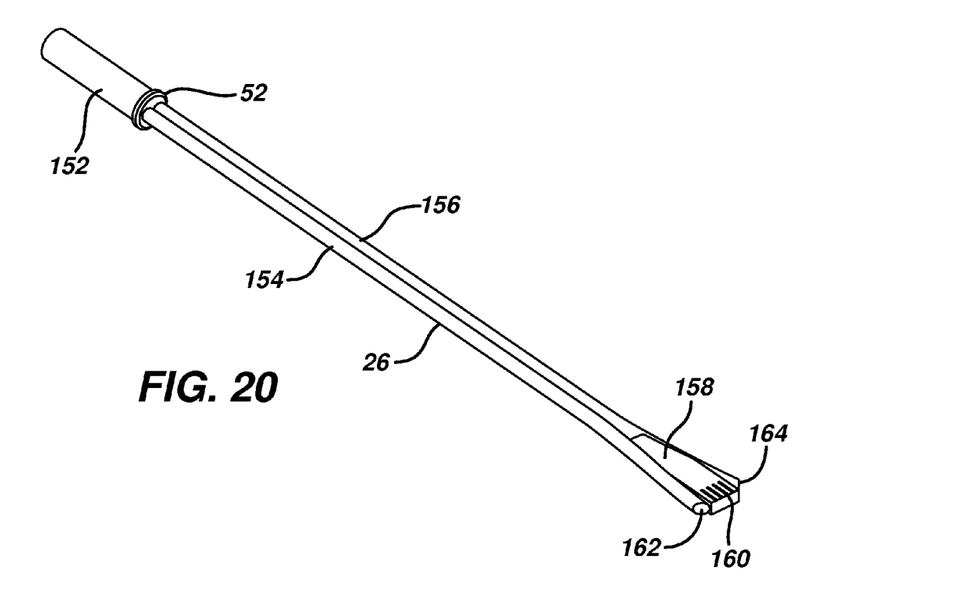
FIG. 20 is a perspective view of an alternative embodiment of an elongate support member and surgical implement for measuring distances arthroscopically.
Figure 21:
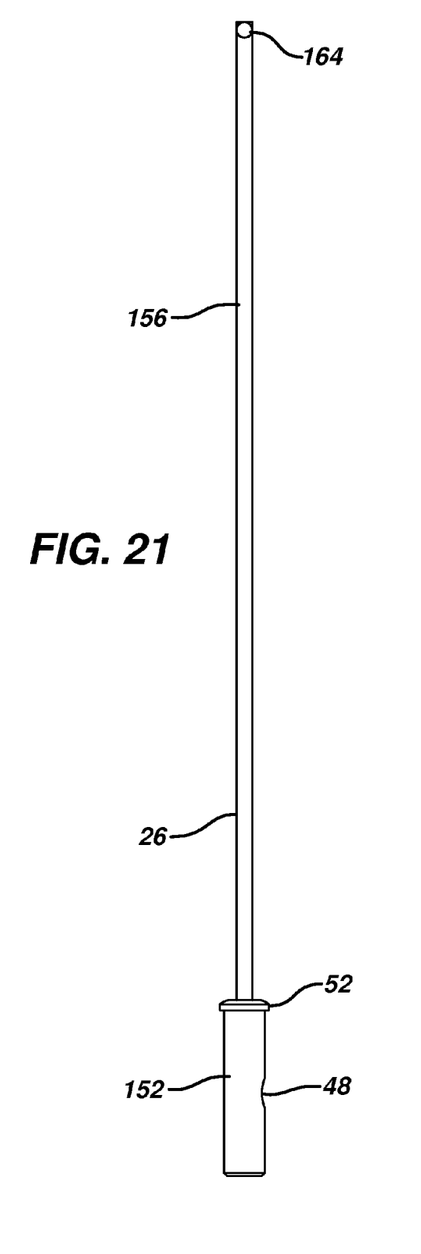
FIG. 21 is an elevation or side view of the elongate support member of FIG. 20.
Figure 22:
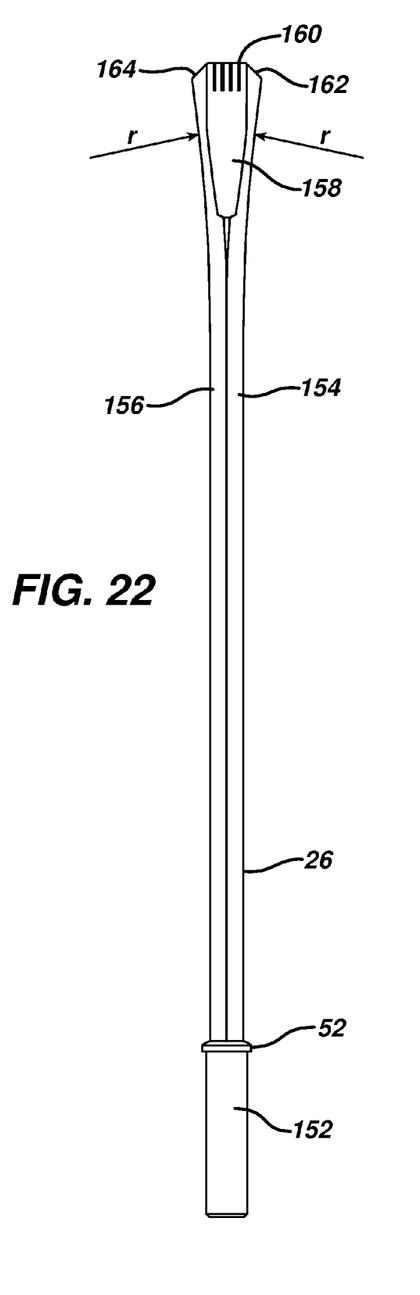
FIG. 22 is a top plan view of the elongate support member of FIGS. 20-21.

As shown in FIGS. 7 and 12, the flat upper and lower surfaces 54, 56 (see FIG. 11) and interior wedge 64 have a distal apex 72 and diverging edges 74, 76 extending from the distal apex 72 in a proximal direction. Preferably, the distal apex 72 comprises a radius rather than a sharp corner to prevent tissue damage as the instrument 10 is introduced to the treatment area during surgery. The junctures of the diverging edges 74, 76 and the curved sidewalls 58, 60 also preferably comprise blend radii. As shown in FIG. 19, the diverging edges 74, 76 each form an angle θ of about 15° with a plane perpendicular to the longitudinal axis of the elongate support member.

The elongate support member 26 in the first illustrated instrument 10 holds a substantial part of the length of the surgical implement 28. The surgical implement 28 illustrated in FIGS. 1-8 comprises a measuring device. The measuring device of the first illustrated instrument 10 allows the surgeon to measure defects at the surgical site, such as the knee or hip, without distortion that may result from use of an arthroscope alone.

As shown in FIGS. 1-6, the measuring device comprises a pair of elongate distance references 78, 80. Both elongate distance references 78, 80 are connected at their proximal ends to the distal end of a slide member 82 in the interior of the body portion 24 of the handle 20 (shown in FIGS. 5-6). From the interior of the handle 20, the distance references 78, 80 extend distally through the cylindrical portion of the elongate support member 26, through the transition portion 62, and through the non-cylindrical portion of the elongate support member. At the wedge 64, the elongate distance references 78, 80 diverge, one extending through one passageway 66 and the other extending through the other passageway 68.

As shown in FIGS. 1-2 and 19, the distance references 78, 80 have a retracted position, wherein only small parts of the distal ends of the distance references extend distally past the distal end 46 of the elongate support member 26. The distance references 78, 80 also have a fully extended position, shown in FIGS. 3-4 and in phantom in FIG. 19, wherein a substantially greater length of the distance references extend outside of the elongate support member. The distance references 78, 80 can be moved between the fully retracted and fully extended positions and can be stopped at any interval between the fully retracted and fully extended positions. The distal ends of the distance references 78, 80 may be rounded as shown in FIG. 19 to limit potential damage to native tissue as the instrument is used during surgery.

As shown in FIG. 19, as the distance references 78, 80 are pushed outward through the passageways 66, 68, the distance references are pushed against interior surfaces of the wedge 64 and the side walls 58, 60 of the elongate support 26 to force the distance references 78, 80 out of the openings 67, 69 at the distal end 46 of the elongate support 26 at an angle β, which generally corresponds with the angle α of the wedge. Preferably, angle β equals about 30-45°. As shown in FIG. 19, the distance references 78, 80 can be used to measure distances ranging from $d_1$ to $d_2$, which would typically range from less than about 5 mm up to about 20 mm.

The distance references 78, 80 should be stiff enough so that they do not sag when fully extended, and flexible enough so that they may bend to fit through the divergent passageways 66, 68 at the distal end of the elongate support member 26 as they are extended and retracted. The distance references 78, 80 are preferably sufficiently elastic so that any deformation to the distance references as they are reciprocated through the passageways 66, 68 is not permanent. The distance references 78, 80 should be made of a material that is non-toxic and capable of being efficiently sterilized. One example of a suitable material is the Nitinol alloy of nickel and titanium, a shaped memory alloy, a commercially available material having a diameter of about 1 mm and a length of about 203 mm in the first instrument 10. Other materials are also expected to be useful as the distance references 78, 80; for example, a monofilament of synthetic polymer such as nylon or other biocompatible material could be used. It should be understood that these materials are provided by way of example only; the present invention is not limited to any particular material, size of material, or characteristic of material unless expressly called for in the claims.

Figure 27:
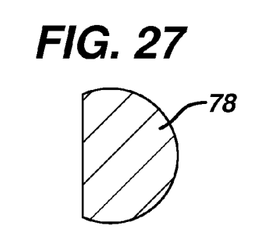
FIG. 27 is a cross-section of a distance reference, showing one possible cross-sectional shape for the distance references.
Figure 28:
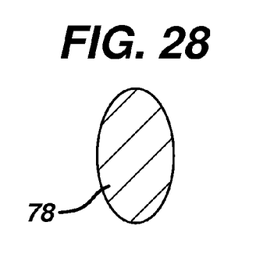
FIG. 28 is a cross-section of a distance reference, showing another possible cross-sectional shape for the distance references.
Figure 29:
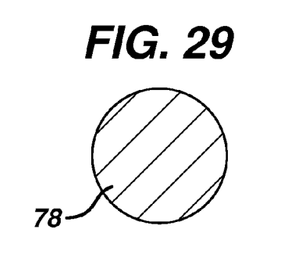
FIG. 29 is a cross-section of a distance reference, showing another possible cross-sectional shape for the distance references.

It should also be understood that the shape of the material used for the distance references 78, 80 could be varied. For example, the distance references could be circular in cross-section, as shown for the distance reference 78 in FIG. 29. To facilitate movement of the distance references from the retracted to the extended positions, a part or all of the outer edges of the distance references could be removed to increase the flexibility of the distance references in one direction so that the distance references have the shape of a truncated circle or a D-shape in cross-section, as shown for the distance reference 78 in FIG. 27; since the outer edges of the distance references are subject to compression during movement of the distance references, removal of part of the bulk of the distance references should increase flexibility. The distance references could also have an oval shape in cross-section, as shown for the distance reference 78 in FIG. 28. It should be understood that the cross-sectional shape of the distance references could vary along their lengths; for example, the shape shown in FIG. 27 might be used along a short segment of the distance references. Accordingly, the present invention is not limited to any particular cross-sectional shape of distance reference unless expressly called for in the claims.

Figure 14:
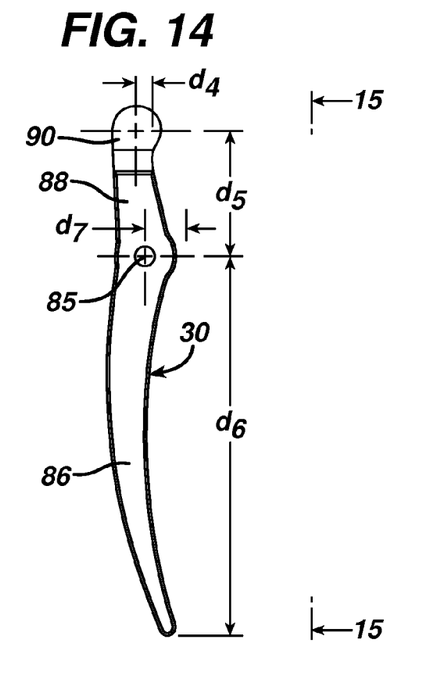
FIG. 14 is an elevation or side view of the lever component of the instruments of FIGS. 1-6 and 8.
Figure 15:
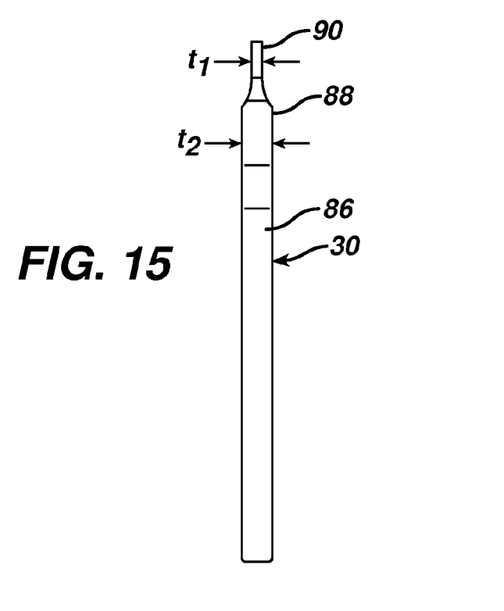
FIG. 15 is an end view of the lever component of FIG. 14, taken along line 15-15 of FIG. 14.

To move the distance references 78, 80 from the retracted to the extended positions, the first instrument provides a lever 30 mounted for relative rotation on the handle 20 on a pin 84. As shown in FIGS. 14-15, the lever 30 includes a trigger portion 86 below a hole 85 to receive the pin 84 and a drive portion 88 above the hole 85. The drive portion 88 includes a cam portion 90 at its top end. As shown in FIG. 14, the center of the cam portion 90 is laterally offset from the center of the hole 85 by a distance of about 2.5 mm in the first instrument, shown at $d_4$ in FIG. 14, and is longitudinally offset by a distance of about 1 inch or 2.5 cm, shown at $d_5$ in FIG. 14. The end of the trigger portion 86 is longitudinally offset from the center of the hole 85 by a distance of 6.8 cm, shown at $d_6$ in FIG. 14, and laterally offset from the center of the hole 85 by a distance of 7 mm, shown at $d_7$ in FIG. 14. As shown in FIG. 15, the cam portion 90 of the lever 30 of the first instrument 10 has a thickness $t_1$ of less than 2 mm; the trigger portion 86 has a thickness $t_2$ of about 5-6 mm. It should be understood that all of the above dimensions are provided as examples only; the present invention is not limited to any particular dimension unless expressly set forth in the claims. Moreover, as described below with respect to the second instrument 12, these dimensions for the lever 30 can be varied; for example, the lateral offset of the cam portion 90 $d_4$ can be increased.

When mounted on the handle 20, the lever 30 is pivotable about the pin 84. The trigger portion 86 can be manipulated by the surgeon to pivot the lever 30. The drive portion 88 is received within the handle 20, and the cam portion 90 is used to effect reciprocal motion of the distance references 78, 80 between the positions shown in FIG. 19.

Figure 13:
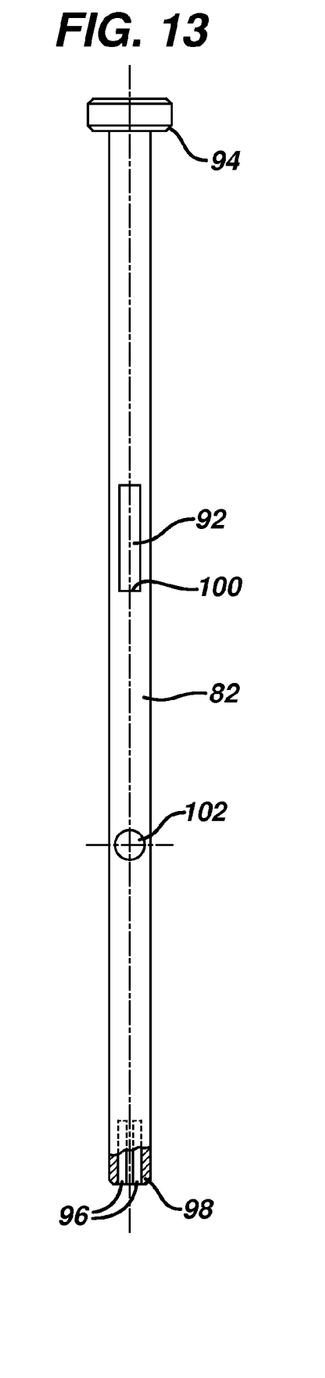
FIG. 13 is an elevation or side view of the slide member used in the instruments of FIGS. 1-6 and 8.

To effect reciprocal motion, the cam portion 90 of the lever 30 is received in a slot 92 of the slide member 82. There is no mechanical connection between the lever 30 and the slide member 82 in the first instrument 10. As shown in FIG. 13, the slide member 82 has a head 94 at its proximal end and receiving structures 96 at its distal end 98 for connection to the distance references 78, 80. In the first instrument 10, the receiving structures 96 comprise channels of slightly larger diameter than the diameters of the distance references 78, 80. Proximal ends of the distance references 78, 80 are received in the channels that comprise the receiving structures 96. The distance references 78, 80 are connected to the slide member through, for example, a press-fit of the distance references 78, 80 in the receiving structures 96, or through the use of an adhesive or mechanical connection, for example; any suitable means can be used for making this connection.

As shown in FIGS. 5-6 and 13, the slide member 82 has a drive surface 100 at the distal end of the slot 92 that is engaged by the cam 90 of the drive portion 88 of the lever 30 to cause the slide member 82 and distance references 78, 80 to reciprocate. As shown in FIG. 13, the slide member 82 also has a hole 102 to receive the indicator pin 38.

The slide member 82 is held within the body portion 24 of the handle 20, and is capable of reciprocal motion in the elongate channel 32 in the proximal-distal direction. The slide member 82, and therefore the distance references 78, 80, are urged in the proximal direction by a spring 104. In the illustrated embodiment, the spring 104 surrounds part of the slide member between the head 94 and a stop in the interior of the body portion 24 of the handle 20. However, the spring could be located elsewhere, such as at or around the distal end 98 of the slide member 82.

As shown in FIGS. 1-6 and 8, a thumb screw 105 is provided at the proximal end 16 of the instrument; the thumb screw 105 bears against the head 94 of the slide member 82 when the slide member and surgical implement 28 are in the retracted position. The retracted position of the slide member 82 and the surgical implement 28 can be adjusted by adjusting the thumb screw 105, so that the zero position of the indicator pin 38 can be adjusted to correspond with the appropriate indicia of the fixed measuring indicia 40, 42.

The second instrument 12, illustrated in cross-section in FIG. 8, is very similar to the first instrument 10, and is useful in making intra-operative measurements arthroscopically. In FIG. 8, the lever designated 30A is shaped differently from the lever 30 of the first instrument 10; the distance $d_4$ is increased by 4 mm to 6.6 mm and the distance $d_5$ is increased by about ½ inch or 12.5 mm to about 1.5 inches or 38 mm. In addition, the potential range of travel for the slide member 82 and the distal ends of the distance references 78, 80 (shown at $d_3$ in FIG. 19) is increased from 20 mm, for example, for the first instrument 10, to 45 mm, for example, for the second instrument 12. With the exception of the lever 30A and its portions, the same reference numbers have been used in the embodiment of FIG. 8 as in the embodiment of FIGS. 1-6; the components of the instrument 12 of FIG. 8 may be like those of the first instrument 10, except as specifically described below.

The overall length of the second instrument 12 is somewhat greater than that of the first instrument 10, allowing for a somewhat larger potential range of travel in the proximal-distal direction. In addition, in the second instrument 12, the slot 36 in which the indicator pin 38 travels is aligned with the slot 34 that receives the lever 30A. This alignment should be advantageous in cleaning the second instrument 12, since the interior of the body portion 24 provides a path for debris travel between the slots 34, 36 and around the portion of the slide member 82 that is in the body 24 between the slots 34, 36.

Figure 16:
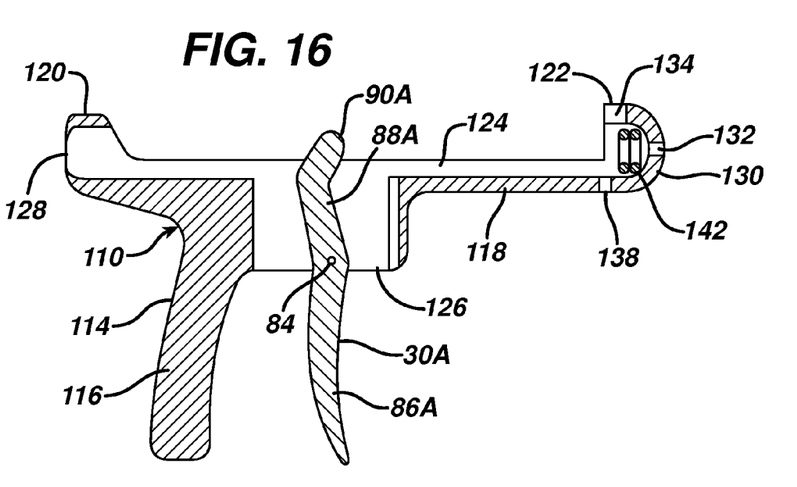
FIG. 16 is a cross-section of an actuator module of a modular instrument embodying the principles of the present invention.
Figure 17:
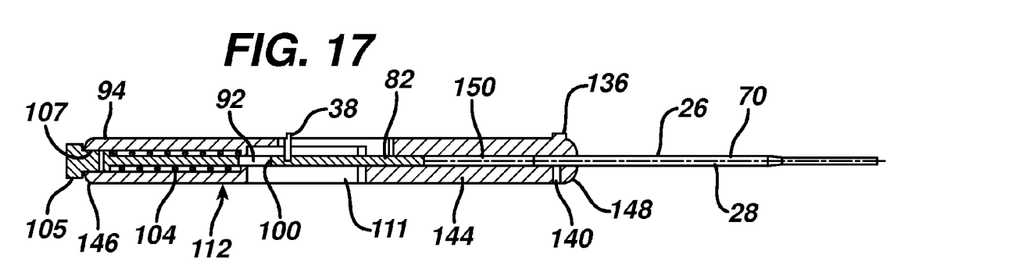
FIG. 17 is a cross-section of a tool module of a modular instrument embodying the principles of the present invention.

The third instrument 14 embodying the principles of the present invention is illustrated in FIGS. 16-18. This instrument 14 can be used like the first two instruments 10, 12, and can have additional uses. The third instrument 14 is a modular one, with an actuator module 110 and a tool module 112.

As shown in FIG. 16, the actuator module 110 includes a handle 114 with a grip portion 116 and an integral support portion 118. The support portion 118 has a proximal end 120 and a distal end 122 and a curved support surface 124 between these two ends 120, 122. The support surface 124 in the illustrated embodiment is concavely curved, and the handle 114 is substantially open above the support surface 124.

The actuator module 110 also includes a lever. In the illustrated embodiment, the lever is shaped like that of the second embodiment 12, and is designated 30A like the lever of the second embodiment. As in the other two embodiments, the lever 30A is pivotally connected to the handle with a pin 84. As in the other embodiments, the lever 30A includes a trigger portion 86A and a drive portion 88A that includes a cam portion 90A. It should be understood that the lever may have a different shape, for example like the shape of the lever 30 of the first embodiment 10. Like the first two embodiments 10, 12, the lever 30A extends through an opening or slot 126 in the support portion 118 of the handle 114. The lever 30A has a reduced thickness at the cam portion 90A.

The proximal end 120 of the support portion 118 of the handle 114 has an annular shape to receive and hold a portion of the tool module 112 with an opening 128 through which part of the tool module may extend. The proximal end 120 may be shaped to restrain proximal movement of the tool module when the instrument is assembled.

The distal end 122 of the support portion 118 of the handle 114 has an end wall 130 with an opening 132 for another part of the tool module 112 and an anti-rotation structure 134 to mate with a similar structure in the tool module to stabilize the position of the tool module. In the illustrated embodiment, the anti-rotation structure comprises a slot to mate with a tab 136 on the tool module, but it should be understood that these complementary structures are provided as an example only. There may also be a through-hole 138 in the support portion of the handle to align with a hole 140 in the tool module to receive a screw similar to screw 50 to lock the modules 110, 112 together in the proper relative position.

In the embodiment illustrated in FIGS. 16 and 18, the actuator module also includes an optional spring 142 retained at the distal end 122. The spring 142 can be provided to assist in constraining proximal-distal movement of the tool module 112 on the actuator module 110 when the modules 110, 112 are assembled.

The tool module 112 illustrated in FIG. 17 has a housing 144 with a proximal end 146 and a distal end 148. The housing 144 is hollow, with a channel 150 extending from the proximal end 146 to the distal end 148. A slide member with features like those of the first two embodiments 10, 12 is received in the channel 150; like reference numbers have been used for the slide member 82 in the third embodiment 14. Also as in the first two illustrated embodiments 10, 12, a spring 104 acts against an integral ledge in the housing to urge the head 94 of the slide member 82 in the proximal direction. The slide member 82 can also have a hole to accept an indicator pin 38 as in the first two embodiments. The housing 144 of the third embodiment 14 can carry fixed measuring indicia (not shown) as in the first two embodiments. A thumb screw 105 can also be provided as in the first two embodiments to set the position of the slide member 82 and indicator pin 38 with respect to the fixed measuring indicia. An entry slot 111 is also provided in the housing 144, through which at least part of the drive portion 88A of the lever 30A can extend.

The tool module 112 also includes a hollow elongate support member 26 and a surgical implement 28. These elements 26, 28 may be like those of the first two illustrated embodiments 10, 12, and like reference numbers have been used in FIGS. 17-18 for similar parts. The above description of these elements 26, 28 also apply to the support member and surgical implement of the embodiment illustrated in FIGS. 17-18. In the embodiment of FIGS. 17-18, the elongate support member 26 is fixed to the distal end of the housing 144 instead of to the handle. In the embodiments of FIGS. 17-18, the channel 150 of the housing and channel 70 of the elongate support member 26 are connected, and the surgical implement extends through both channels 150, 70.

As in the first two described embodiments, the surgical implement 28 of the third embodiment 14 is capable of reciprocal motion in the proximal-distal direction relative to the hollow elongate support member 26, and at least part of the surgical implement 28 extends out through an opening in the distal end of the elongate support member 26 at least part of the time.

Figure 25:
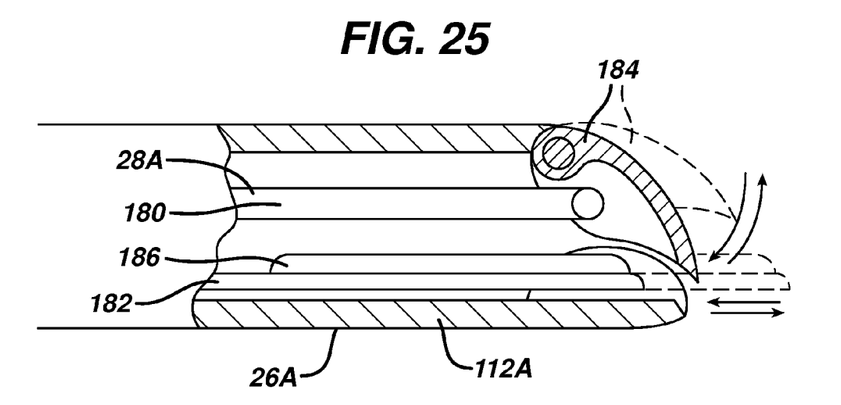
FIG. 25 is a cross-section of the distal end of an elongate support member of an alternate tool module, with the retracted position of the surgical implement shown in solid and the extended position shown in phantom.
Figure 26:
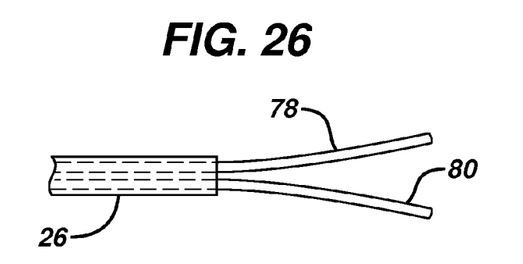
FIG. 26 is a top plan view of the distal end of an elongate support member with shaped memory distance references pre-formed to diverge outwardly.

In the third illustrated embodiment, the tool module 112 comprises a cartridge that can be easily and quickly assembled with the actuator module 110, and easily and quickly disassembled. Thus, either the actuator module 110 or the tool module 112 can be made to be disposable. In addition, a plurality of tool modules could be included as part of a kit that includes the actuator module 110; the plurality of tool modules could all comprise measurement devices, as illustrated in FIGS. 1-8 and 17-19, or could comprise other types of tools as well. Examples of other tool modules are illustrated in FIGS. 25-26.

All of the above embodiments can be used with alternative surgical implements and with alternative elongate support members. An alternative design for a distance measuring implement is illustrated in FIGS. 20-24. As there shown, the elongate support member 26 comprises a proximal cylindrical portion 152 to be received in the handle 20 or cartridge housing 144 and a pair of discrete, hollow elongate tubes 154, 156 extending distally from the cylindrical portion 152 to the distal end of the elongate support member 26. The support member 26 of the embodiment of FIGS. 20-24 has an annular stop 52 at the junction of the cylindrical portion 152 and the discrete tubes 154, 156, as in the first embodiment. The discrete tubes 154, 156 are substantially parallel to each other for a substantial part of their lengths, and diverge outwardly at their distal ends.

In this embodiment, the shapes of the distal ends of the discrete tubes 154, 156 are defined by a wedge 158 interposed between them. The wedge 158 has exposed top and bottom surfaces, which include distance indicia 160 in the illustrated embodiment. The distance indicia 160 may be printed or etched parallel lines spaced at equal distances of, for example, 1 mm so the surgeon can use the distance indicia 160 to measure small defects.

In the embodiment of FIGS. 20-24, the wedge is shaped so that the distal ends of the discrete tubes 154, 156 curve outwardly. In the illustrated embodiment, the distal ends of the discrete tubes 154, 156 are each curved outwardly at a radius of curvature of about 15 cm. (5.9 inches), shown at "r" in FIG. 22. It should be understood that this radius is provided by way of example only, and the present invention is not limited to use of curved tubes or to use of tubes curved at this radius unless expressly called for in the claims.

In the embodiment of FIGS. 20-24, the discrete tubes 154, 156 have beveled ends 162, 164 so that the tubes 154, 156 are longest along their innermost edges. With the ends so shaped, more precise measurement of a defect using the distance indicia 160 is possible. It should be understood that the present invention is not limited to use of such beveled ends unless expressly called for in the claims.

Figure 23:
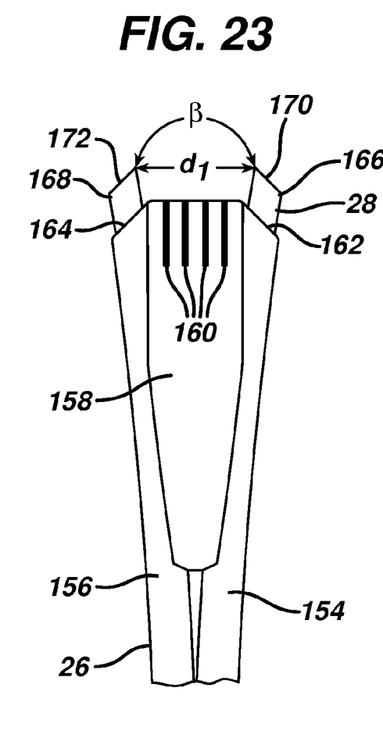
FIG. 23 is an enlarged top plan view of the distal end of the elongate support member of FIGS. 20-22, with the distance references in a retracted position.
Figure 24:
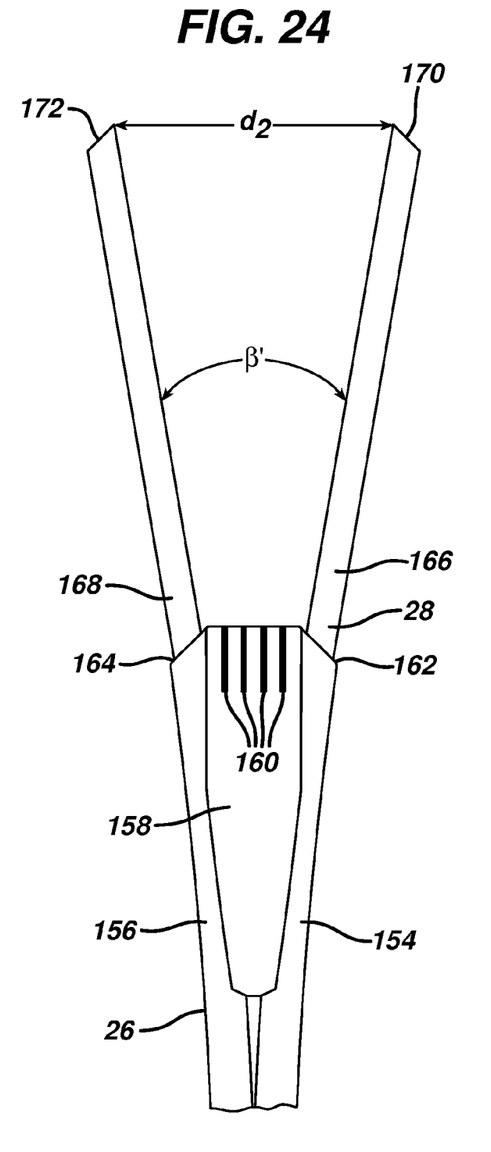
FIG. 24 is an enlarged top plan view of the distal end of the elongate support member of FIGS. 20-22, with the distance references in an extended position.

As in the first illustrated embodiment, the embodiment of FIGS. 20-24 includes a pair of elongate distance references 166, 168. The distance references 166, 168 may be made of the materials described above for the distance references 78, 80 and may be similarly sized. These distance references 166, 168 may have various cross-sectional shapes, such as any of those illustrated in FIGS. 27-29, along all or part of their lengths. Like the distance references 78, 80, the elongate distance references 166, 168 are capable of reciprocal movement in the elongate support member 26. Two possible positions of the elongate distance references 166, 168 are illustrated in FIGS. 23-24. In FIG. 23, the elongate distance references 166, 168 are shown in a retracted position to measure a distance $d_1$; in FIG. 24, the elongate distance references 166, 168 are shown in an extended position to measure a distance $d_2$. In both illustrated positions, the distance references 166, 168 are separated by an angle shown at $\beta$ and $\beta'$ in FIGS. 23-24; $\beta$ and $\beta'$ can be expected to be substantially equal, although there may be some difference due to the curvature imparted to the elongate distance references 166, 168 by the shapes of the tubes 154, 156. The distance references 166, 168 can be moved to positions between those shown in FIGS. 23-24 to measure distances between $d_1$ and $d_2$.

To enable more precise measurements, the distance references 166, 168 in the embodiment of FIGS. 20-24 have beveled ends 170, 172. As shown in FIGS. 23-24, the beveled ends 170, 172 are shaped so that the distance references are longest along their inner edges. Thus, the size of a defect, such as a meniscal defect, can be measured by moving the distance references 166, 168 distally or proximally until the longest parts of the beveled ends 170, 172 are aligned with the ends of the defect to be measured.

It should be understood that if a shaped memory material is used for the distance references 78, 80, 166, 168, the distance references could be pre-formed or pre-shaped to have a bend or radius as shown in FIG. 26, so that the distance references have an unstressed shape corresponding with the fully extended position. Retracting the distance references into the support member 26 would temporarily straighten the distance references, but the distance references would return to their pre-form or pre-shape shown in FIG. 26 when extended without use of a wedge or divergent pathways to guide the distance references.

For any of the illustrated embodiments, surgical implements other than measuring devices could be used. For example, the surgical implement could be used for grasping, grabbing, cutting or injecting, for example; the surgical implement could comprise any arthroscopic device that can be operated by reciprocal motion. Examples of such surgical implements are illustrated and described in various surgical texts, such as O'CONNOR's TEXTBOOK OF ARTHROSCOPIC SURGERY, $2^{nd}$ ed. 1992, Chapter 19, which is incorporated by reference herein. Whatever form of surgical implement used, the implement could be used in conjunction with an instrument such as those illustrated in FIGS. 1-6 and 8, or could be part of a cartridge-type device such as that illustrated in FIGS. 17-18.

The present invention could also be used to deliver implants to the site of a defect. An example of such a surgical implement for a surgical instrument is illustrated in FIG. 25 as a tool module. In the tool module 112A of the embodiment of FIG. 25, the surgical implement 28A comprises a pair of rods or tangs 180, 182 carried in a cylindrical elongate support member 26A. The proximal end of each rod or tang 180, 182 is connected to the distal end of the slide member 82 in the housing 144 (not shown) as in the above-described embodiments. As in the above-described embodiments, the rods or tangs 180, 182 can be reciprocated by operation of the lever 30, 30A. In the embodiment of FIG. 25, the distal end of one rod or tang 180 is pivotally connected to a cover member 184 that is pivotally connected to the elongate support member 26A; the distal end of the other rod or tang 182 may be temporarily connected to an implant by means of suture for example. When the rods or tangs 180, 182 are in the retracted position, shown in FIG. 25, the cover member extends over and protects the implant, shown at 186 in FIG. 25 so that the implant can be moved arthroscopically to the desired position in the body. When the trigger portion of the lever is pulled, the rods or tangs 180, 182 are pushed distally, causing the cover member 184 to pivot upward and the implant 186 to be pushed out of the support member 26A so that the surgeon can attach the implant at the desired location in the body.

To assemble the instruments, the proximal ends of the elongate distance references 78, 80 or rods or tangs 180, 182 may be connected to the distal end of the slide member 82. The elongate support member 26, 26A may be assembled with the body portion 24 of the handle 20 or the housing 144 by inserting the proximal end of the elongate support member 26 into the hole at the distal end of the handle or housing until the annular stop 52 abuts the distal end of the handle or housing. The spring 104 is placed on the slide member 82, and the sub-assembly of the spring 104, slide member 82 and distance references 78, 80 or rods or tangs 180, 182 is pushed through the opening 107 at the proximal end of the handle or cartridge housing 144. The sub-assembly is pushed distally to push the distance references 78, 80 or rods or tangs 180, 182 through the channel 32 in the body (or channel 150 of the housing) and through the channel 70 of the elongate support member 26, 26A to the distal end of the elongate support member 26, 26A. At this point, the head 94 of the slide member 82 should be received fully within the handle or housing, and the thumb screw 105 may be screwed onto the threaded end of the handle or housing to retain the slide member 82 in position. If the surgical implement is a distance measuring device, the indicator pin 38 may be affixed to the hole 102 of the slide member 82 by placing the pin 38 through the top slot 36.

For the third embodiment 14, the tool module 112 can be assembled by attaching the proximal end of the surgical implement to the distal end of the slide member, placing the spring on the slide member, and then inserting this sub-assembly through the opening at the distal end of the housing. The thumb screw 105 can then be threaded in place to hold the assembly together. For a measuring implement, the indicator pin 38 can be placed through the top slot in the housing into the hole 102 in the slide member 82 and affixed therein by conventional means.

The actuator module can be assembled simply by connecting the lever 30, 30A to the handle through a pivot pin 84. If desired, the spring can be placed at either the proximal or distal end of the handle. The actuator module and tool module can then be assembled by placing the housing 144 of the tool module 112 between the ends 120, 122 of the handle and inserting the lever as described above.

Assembly of the lever 30, 30A with the slide member 82 is simple in each of the embodiments 10, 12, 14. For the first two embodiments, 10, 12, when the slide member 82 is in position in the handle or the housing, the slot 92 in the slide member 82 is visible from the underside of the handle by looking through the lever slot 34. The lever 30, 30A can be assembled with the slide member 82 by inserting the drive portion 88, 88A of the lever 30, 30A through the entry slot 34 until the cam portion 90, 90A of the lever 30, 30A is received within the slot 92 of the slide member 82. The lever 30, 30A is then pivotally connected to the handle by inserting pivot pin 84. For a measuring device, the thumb screw 105 may then be adjusted so that the indicator pin 38 aligns with the zero mark on the fixed measuring indicia 40, 42. The instrument is then ready to be used.

For the modular embodiment 14 of FIGS. 16-18, prior to assembly, the slot 92 in the slide member 82 is visible through the entry 111 slot in the bottom of the housing 144 so the drive portion 88A of the lever 30A can be easily guided through this housing entry slot 111 and into the slide member slot 92 as the tool module 112 and actuator module 110 are pushed together. With the cam portion 90A of the lever 30A of the actuator module 110 aligned to be received in the slide member slot 92, the two modules 110, 112 can be pushed together until the housing 144 is supported by the concave support structure 118 and movement is constrained by the retaining structures at the proximal and distal ends 120, 122 of the handle. Rotation of the tool module 112 is constrained by structures such as the complementary structures shown at 134, 136 in FIGS. 16-18. A screw can be placed in the aligned holes 138, 140 and into the groove or socket 48 of the elongate support member 26A to lock the three components 110, 112, 26A together. Alternatively, a screw could be used to merely lock the housing 144 and elongate support member 26A together.

Assembly of other tool modules with other surgical implements is similar to that described above for the distance measuring implement.

In use, the surgeon can perform standard arthroscopic procedures to create portals at the affected area of the patient. Standard cannulae can be inserted through the portals. The elongate support portion 26, 26A of any of the illustrated surgical tools can be inserted into one of the cannula and moved into the field of vision of an arthroscope received in another cannula. The distal end of the elongate support can be moved to the affected area, such as a defect in the meniscus. The surgeon can squeeze the trigger portion 86, 86A of the lever proximally causing the cam portion 90, 90A of the lever 30, 30A to pivot distally against the drive surface 100 of the slot 92 of the slide member 82, thereby causing the distance references 78, 80, 166, 168 or rods or tangs 180, 182 to move distally.

The effect of distal movement of the elements 78, 80, 166, 168, 180, 182 depends upon the structure of the surgical implement. If the surgical implement is a distance measuring device, the distance references can be moved distally until their ends are aligned with the ends of a defect in the body and the dimension of the defect can be read from the position of the indicator pin 38 along the fixed measuring indicia 40, 42. If the surgical implement is an implant delivery implement, the surgeon can insert the elongate support 26A until its distal end is at or near the defect site while protecting the implant from damage; the surgeon can then operate the lever 30A to move the elements 180, 182 distally to open the distal end of the elongate support and push the implant distally out of the elongate support so that the surgeon can then attach the implant in the normal fashion.

While the illustrated embodiments of the present invention can be assembled and then sterilized for use, these embodiments are advantageous in that components or sub-assemblies can be sterilized separately and then final assembly made in the operating room at the point of use.

While only specific embodiments of the invention have been described and shown, it is apparent that various alternatives and modifications can be made thereto. Those skilled in the art will also recognize that certain additions can be made to the illustrative embodiments. It is, therefore, the intention in the appended claims to cover all such alternatives, modifications and additions as may fall within the true scope of the invention.

We claim:

1. A surgical instrument having a proximal end and a distal end, the surgical instrument comprising:

a handle at the proximal end, the handle including a grip portion;

a hollow elongate support member extending distally from the handle and having a distal end at the distal end of the surgical instrument;

a slide member having a proximal end, a distal end, a drive surface and a through-slot at the drive surface between the two ends, the through-slot extending in a proximal-distal direction and being spaced from distal end of the hollow elongate support member;

a lever connected to the handle at a pivotal connection, the lever including a lever grip portion on one side of the pivotal connection and an integral drive portion on the other side of the pivotal connection, at least part of the drive portion comprising an integral cam received in the through-slot in the slide member adjacent to the drive surface;

a surgical implement having a proximal end connected to the distal end of the slide member, an elongate portion extending through the hollow elongate support, and a distal end;

a spring to urge the slide member toward the proximal end of the surgical instrument;

wherein the slide member and elongate portion of the surgical implement are capable of being moved in a linear distal direction by pivoting the lever so that the integral cam of the lever pushes against the drive surface of the slide member;

wherein the surgical instrument is free of any mechanical connection between the lever and the slide member;

the surgical instrument further comprising a housing around at least a portion of the slide member, wherein the elongate support member and surgical implement extend outward from the housing, and wherein the housing, slide member, elongate support member and surgical implement comprise a cartridge removable from the handle and lever.

2. The surgical instrument of claim 1 wherein the housing has a proximal opening aligned with the slide member, a channel extending distally from the proximal opening, and an entry slot in communication with the channel, wherein the elongate portion of the surgical implement and slide member can be assembled into a subassembly by connecting the elongate portion of the surgical implement to the slide member, and wherein the cartridge can be assembled by inserting the subassembly through the proximal opening in the housing, inserting the drive portion of the lever through the entry slot in the housing and into the through-slot in the slide member, and pushing the elongate portion of the surgical implement through the elongate support member.

3. A modular surgical instrument comprising an actuator module and a discrete tool module, the actuator module comprising:

a handle comprising a grip portion and an integral support portion, the support portion having proximal and distal ends and a support surface between the proximal and distal ends, the handle being substantially open above the support surface; and a lever pivotally connected to the support portion of the handle, the lever including a trigger portion and a drive portion, the trigger portion being longer than the drive portion, the drive portion extending through an opening in the support surface of the handle; and the tool module comprising an assembly of a hollow housing, a discrete hollow elongate support member, a discrete surgical implement and a discrete slide member;

the hollow housing having proximal and distal ends and being sized and shaped to fit between the proximal and distal ends of the support portion of the handle;

the hollow elongate support member being fixed to the distal end of the housing, the hollow elongate support member having a proximal end within the housing and extending outwardly from the housing to a free distal end, the free distal end having an opening;

the hollow housing and hollow elongate support member defining an open passageway between them;

the surgical implement being capable of reciprocal motion in the proximal-distal direction relative to the hollow elongate support member, at least part of the surgical implement extending through the hollow elongate support member and out through the opening at the free distal end of the elongate support member, the surgical implement having a proximal part extending past the proximal end of the hollow elongate support member into the housing; and the slide member being operably connected to at least part of the surgical implement and being capable of reciprocal motion in the proximal-distal direction relative to the housing, the slide member having a drive surface within the housing;

wherein the actuator module and tool module are capable of being assembled and disassembled so that at least one of the modules can be reused independent of the other module, and wherein when the actuator module and tool module are assembled the drive portion of the lever engages the drive surface of the slide member so that the slide member and surgical implement can be moved in the distal direction by squeezing the trigger portion of the lever.

4. The modular surgical instrument of claim 3 wherein the slide member has an elongate slot and the housing of the tool module has an opening aligned with the elongate slot so that the actuator module and tool module can be assembled by inserting the drive portion of the lever through the opening in the housing of the tool module and into the elongate slot in the slide member.

5. The modular surgical instrument of claim 3 wherein the surgical implement comprises a pair of elongate substantially flexible distance references connected at one end to the slide member in the housing and extending out of the free distal end of the elongate support member.

6. The modular surgical instrument of claim 5 wherein the free distal end of the elongate support member has substantially flat upper and lower surfaces and an interior wedge between the substantially flat upper and lower surfaces, the interior wedge diverging in the distal direction and defining two divergent passageways, and wherein one of the elongate substantially flexible distance references extends through one of the divergent passageways of the elongate support member and the other of the elongate substantially flexible distance references extends through the other of the divergent passageways of the elongate support member.

7. The modular surgical instrument of claim 3 wherein the surgical implement comprises a pair of elongate distance references connected at one end to the slide member in the housing and extending out of the free distal end of the elongate support member to free ends, the elongate distance references being made of a shape memory material and the free ends being divergent.

8. The modular surgical instrument of claim 3 wherein the surgical implement comprises an elongate rod and a tissue manipulator, wherein the elongate rod is received in the elongate support member and connected at one end to the slide member and at the other end to the tissue manipulator.

9. The modular surgical instrument of claim 3 wherein the surgical implement comprises a cannula, wherein the cannula is received in the elongate support member and connected at one end to the slide member.

10. The modular surgical instrument of claim 3 wherein the actuator module and the tool module define separate elements of a kit.

11. The modular surgical instrument of claim 10 wherein the kit includes a plurality of tool modules.

12. The modular surgical instrument of claim 3 wherein the handle is sized and shaped to support the housing of the tool module and to limit relative proximal-distal movement between the housing of the tool module and the handle.

13. The modular surgical instrument of claim 3 wherein at least one of the actuator module and tool module includes a spring for urging the slide member toward the proximal end of the housing.

14. A disposable surgical tool module for use with a separate actuator module, the surgical tool module comprising:
   a hollow housing having proximal and distal ends and a channel extending between the ends;
   a discrete hollow elongate support member at the distal end of the housing, the hollow elongate support member having a proximal end received within the housing, the hollow elongate support member extending outwardly from the housing to a free distal end, the free distal end having an opening, the hollow elongate support member having an axial length between the proximal and distal ends, a majority of the axial length of the hollow elongate support member being exposed outside of the housing;
   a surgical implement having a proximal end within the housing, at least part of the surgical implement extending through the hollow elongate support member and out through the opening at the free distal end of the hollow elongate support member, the hollow elongate support member being sized and shaped to allow linear movement of the surgical implement in the proximal and distal direction; and
   a slide member held within the housing and operably connected to the proximal end of the surgical implement between the proximal end of the housing and the proximal end of the hollow elongate support member, the channel of the housing being sized and shaped to allow linear movement of the slide member in the proximal and distal directions in the channel, the slide member having a slot within the housing, the slot having an axial dimension and a transverse dimension, the axial dimension being greater than the transverse dimension;
   the housing having an opening aligned with the slot of the slide member, the opening in the housing having an axial dimension greater than the axial dimension of the slot;
   the tool module being free from any structure for moving the slide member in the distal direction.

15. The disposable surgical tool module of claim 14 wherein the surgical tool module comprises part of a kit, the kit further including an actuator module including a handle for receiving and supporting the housing of the surgical tool module and a lever pivotally attached to the handle.

16. The disposable surgical tool module of claim 14 wherein the surgical implement comprises at least one of the following:
   a pair of elongate substantially flexible distance references connected at one end to the slide member in the housing and extending out of the free distal end of the elongate support member;
   an elongate rod and a tissue manipulator, wherein the elongate rod is received in the elongate support member and connected at one end to the slide member and at the other end to the tissue manipulator; and
   a cannula connected at one end to the slide member.

17. The disposable surgical tool module of claim 14 further comprising a spring in the housing for urging the slide member toward the proximal end of the housing.

18. The disposable surgical tool module of claim 14 wherein the free distal end of the elongate support member has substantially flat upper and lower surfaces and an interior wedge between the substantially flat upper and lower surfaces, the interior wedge diverging in the distal direction and defining two divergent passageways, and wherein the surgical implement comprises a pair of elongate substantially flexible distance references, wherein each distance reference extends through one of the divergent passageways of the elongate support member.

19. The disposable surgical tool module of claim 14 wherein the surgical implement comprises a pair of elongate distance references connected at one end to the slide member in the housing and extending out of the free distal end of the elongate support member to free ends, the elongate distance references being made of a shape memory material and having at least one of the following unstressed shapes: substantially straight and parallel; and divergent at the free ends.

* * * * *